US012694968B2

(12) United States Patent
Vaughan et al.

(10) Patent No.: US 12,694,968 B2
(45) Date of Patent: Jul. 28, 2026

(54) AUTOMATED RESPITE BEACON BASED ON IDENTIFIED USER CONDITION AND IDENTIFIED USER CONTEXT

(71) Applicant: Express Scripts Strategic Development, Inc., St. Louis, MO (US)

(72) Inventors: Moses Vaughan, Nutley, NJ (US); Sahaya Chitra Arputham, Cumming, GA (US); Mahsa Shateri, Los Angeles, CA (US); Bill Loi Pham, Highlands Ranch, CO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 167 days.

(21) Appl. No.: 18/541,226

(22) Filed: Dec. 15, 2023

(65) Prior Publication Data

US 2025/0201382 A1 Jun. 19, 2025

(51) Int. Cl.
*G16H 20/70* (2018.01)

(52) U.S. Cl.
CPC .................................. *G16H 20/70* (2018.01)

(58) Field of Classification Search
CPC ...................................................... G16H 20/70
See application file for complete search history.

(56) References Cited

U.S. PATENT DOCUMENTS

| | | | |
|---|---|---|---|
| 9,594,793 B2 | 3/2017 | Dantzig | |
| 9,641,991 B2 | 5/2017 | Pitis | |
| 10,235,996 B2 | 3/2019 | Renard | |
| 10,249,095 B2 | 4/2019 | Energin | |
| 10,477,342 B2 * | 11/2019 | Williams | A63F 9/12 |
| 10,481,994 B2 | 11/2019 | Terho | |
| 10,684,910 B2 | 6/2020 | Chau | |
| 10,929,468 B2 | 2/2021 | Imai | |
| 2014/0007197 A1 | 1/2014 | Wray | |
| 2015/0297140 A1 * | 10/2015 | Hernandez | A61B 5/165 |
| | | | 600/587 |
| 2016/0234572 A1 * | 8/2016 | Dixit | G08B 21/0423 |
| 2017/0004260 A1 * | 1/2017 | Moturu | G16H 10/60 |
| 2017/0221480 A1 | 8/2017 | Tzirkel-Hancock | |
| 2017/0329466 A1 | 11/2017 | Krenkler | |
| 2019/0045020 A1 * | 2/2019 | Ein-Gil | A61B 5/165 |
| 2020/0042086 A1 * | 2/2020 | Bastide | G06F 3/017 |
| 2020/0205746 A1 * | 7/2020 | Burwinkel | G08B 21/0446 |

(Continued)

OTHER PUBLICATIONS

Yekta Said Can et. al., Stress detection in daily life scenarios using smart phones and wearable sensors: A survey, Journal of Biomedical Informatics, vol. 92, 2019, 103139, (Year: 2019).*

(Continued)

*Primary Examiner* — Anne-Marie K Alderson
(74) *Attorney, Agent, or Firm* — Jordan IP Law PC

(57) ABSTRACT

Apparatuses, systems, and methods relate to technology to receive first data and second data from an internet-of-things device associated with a user, where the first data includes a measurement of the user. The technology also determines a user condition based on the received first data, determines a context associated with the user condition based on the received second data, determines a first action to mitigate the user condition based on the context, and provides the first action to a user device associated with the user, wherein the user device is to execute the first action.

20 Claims, 11 Drawing Sheets

(56) References Cited

U.S. PATENT DOCUMENTS

| | | | | |
|---|---|---|---|---|
| 2020/0368488 | A1* | 11/2020 | Sato | G04G 13/025 |
| 2021/0000403 | A1* | 1/2021 | Xu | H04M 1/72451 |
| 2022/0313223 | A1* | 10/2022 | Thigpen | A61B 5/0816 |
| 2022/0384034 | A1* | 12/2022 | Hurwitz | G06N 20/10 |
| 2023/0081359 | A1* | 3/2023 | Mirtaheri | G16H 40/67 |
| | | | | 600/300 |
| 2023/0099519 | A1* | 3/2023 | Beltran | G16H 50/20 |
| | | | | 600/300 |
| 2023/0329631 | A1* | 10/2023 | de Zambotti | A61B 5/4809 |
| 2024/0071201 | A1* | 2/2024 | Teachman | G16H 15/00 |
| 2024/0164672 | A1* | 5/2024 | Pasley | G06F 3/015 |

OTHER PUBLICATIONS

Donato, Autonomic nervous system, https://qbi.uq.edu.au/brain/brain-anatomy/peripheral-nervous-system/autonomic-nervous-system, accessed as early as May 17, 2023.
Farnsworth, Heart Rate Variability—How to Analyze ECG Data,https://imotions.com/blog/learning/best-practice/heart-rate-variability/, Jul. 19, 2019.
Felman, What to know about anxiety, https://www.medicalnewstoday.com/articles/323454, as early as May 17, 2023.
Foursquare, Places API, https://docs.foursquare.com/developer/reference/places-api-overview, accessed as early as May 17, 2023.
Frieswick, Measuring HRV to Manage Stress on the Job, https://blog.totalbrain.com/measuring-hrv-to-manage-stress-on-the-job, Jan. 31, 2022.
Harvard Health Publishing Staff, Heart rate variability: How it might indicate well-being, https://www.health.harvard.edu/blog/heart-rate-variability-new-way-track-well-2017112212789, accessed as early as May 17, 2023.
Held, et al. "Heart rate variability change during a stressful cognitive task in individuals with anxiety and control participants." BMC psychology 9 (2021): 1-8. https://bmcpsychology.biomedcentral.com/articles/10.1186/s40359-021-00551-4.
Peterson, High Heart Rate Warning on Your Apple Watch? Here's What That Means, https://watchos. gadgethacks.com/how-to/high-heart-rate-warning-your-apple-watch-heres-what-means-0191216/, Dec. 14, 2018.
Sawh, Stress wearables: best devices that monitor stress and how they work, https://www.wareable.com/health-and-wellbeing/stress-monitoring-wearables-explained-7969, Nov. 14, 2022.
Team BestTime, BestTime beginners guide—Part 1 Website tools, https://blog.besttime.app/foot-traffic-nightlife-bars/, Apr. 22, 2021.
Team BestTime, BestTime beginners guide—Part 2 Software API, https://blog.besttime.app/beginners-guide-foot-traffic-data-software-api/, Apr. 27, 2021.
Whoop, Everything You Need to Know About Heart Rate Variability (HRV), https://www.whoop.com/us/en/thelocker/heart-rate-variability-hrv/, Aug. 11, 2021.

* cited by examiner

FIG. 1A

Pause your activities. It is time to go for a walk! Follow this path!

Server 112

First Action 118

100

124

102

104

106

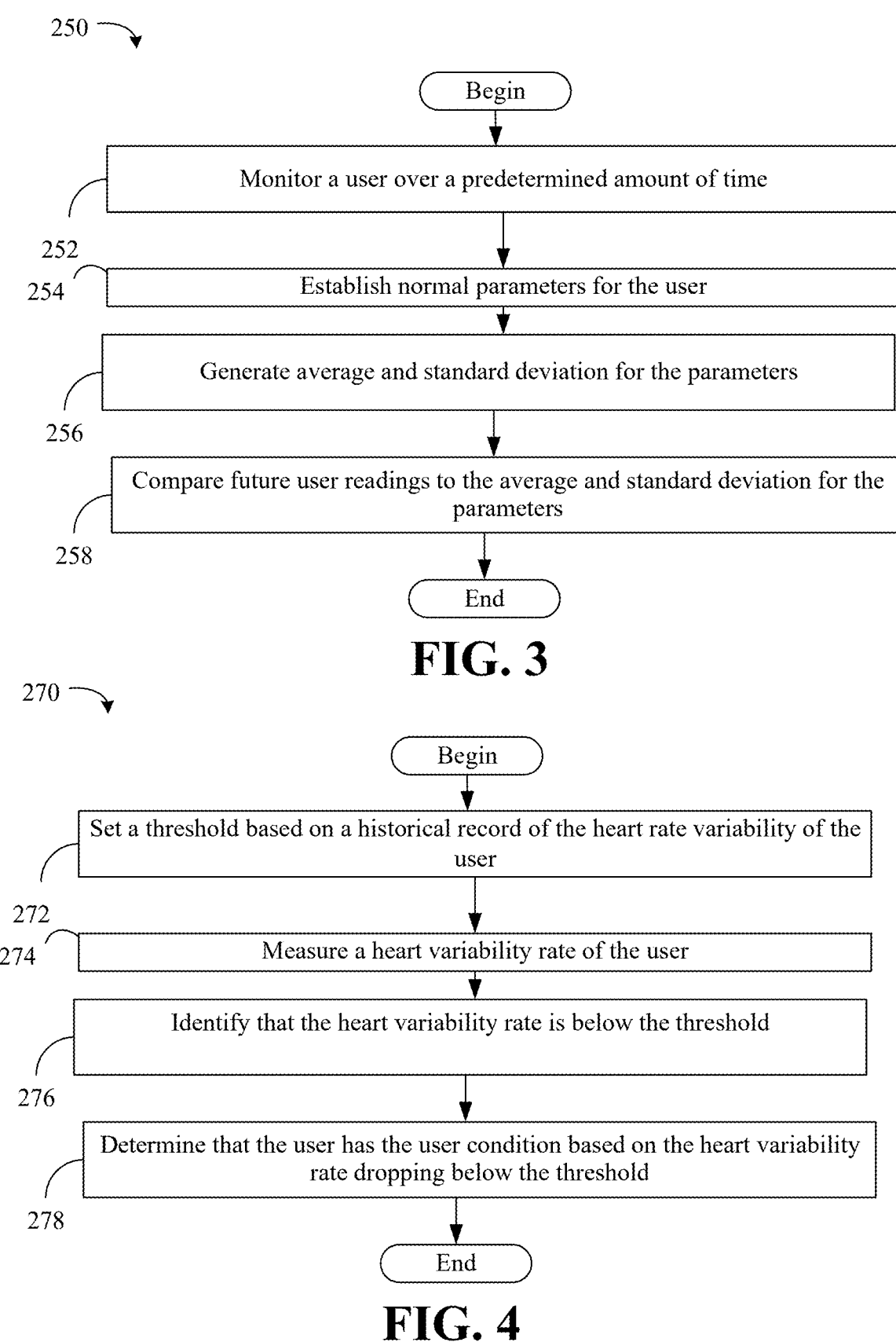

250

Begin

Monitor a user over a predetermined amount of time

252

254  Establish normal parameters for the user

Generate average and standard deviation for the parameters

256

Compare future user readings to the average and standard deviation for the parameters

258

End

Begin

Set a threshold based on a historical record of the heart rate variability of the user

272

274  Measure a heart variability rate of the user

Identify that the heart variability rate is below the threshold

276

Determine that the user has the user condition based on the heart variability rate dropping below the threshold

278

End

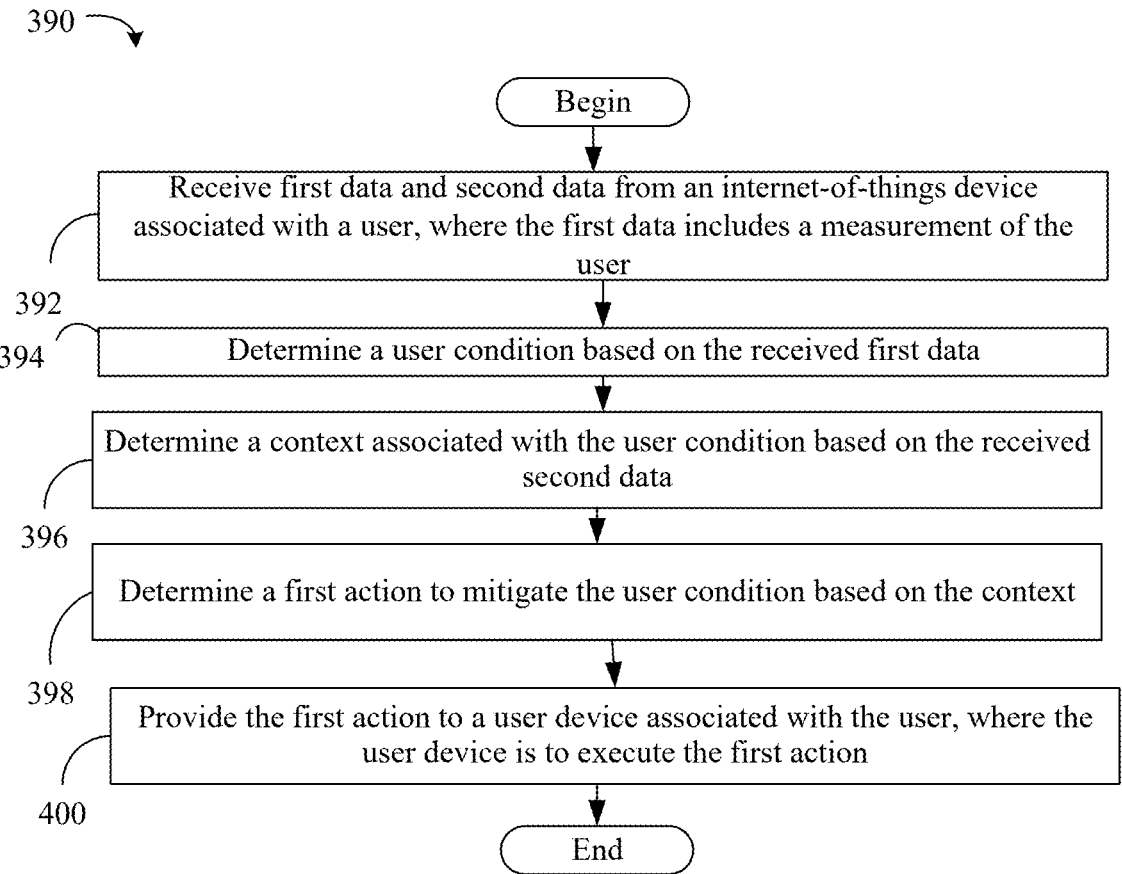

Begin

Receive first data and second data from an internet-of-things device associated with a user, where the first data includes a measurement of the user

392

394    Determine a user condition based on the received first data

Determine a context associated with the user condition based on the received second data

396

Determine a first action to mitigate the user condition based on the context

398

Provide the first action to a user device associated with the user, where the user device is to execute the first action

400

End

FIG. 11

AUTOMATED RESPITE BEACON BASED ON IDENTIFIED USER CONDITION AND IDENTIFIED USER CONTEXT

TECHNICAL FIELD

The present disclosure relates to an enhanced system to provide respite to users. More particularly, examples relate to an automated system that executes in real time to analyze characteristics of a user, determine whether the user is or potentially will experience a negative emotional state, and provide an action to a user device associated with the user to mitigate the negative emotional state.

BACKGROUND

Mental health problems include anxiety disorders. Anxiety disorders refer to a group of mental disorders characterized by feelings of anxiety and fear, including generalized anxiety disorder (GAD), panic disorder, phobias, social anxiety disorder, obsessive-compulsive disorder (OCD) and post-traumatic stress disorder (PTSD). As with depression, symptoms can range from mild to severe. Such anxiety disorders can have physical symptoms such as sweating, trembling, dizziness or a rapid heartbeat. Mental health problems can result in significant lost productivity, have negative emotional consequences (e.g., depression, sadness, etc.) and cause detrimental physical manifestations (e.g., high blood pressure, ulcers, etc.).

BRIEF DESCRIPTION OF THE SEVERAL VIEWS OF THE DRAWINGS

The various advantages of the examples of the present disclosure will become apparent to one skilled in the art by reading the following specification and appended claims, and by referencing the following drawings, in which:

Figure 1A:
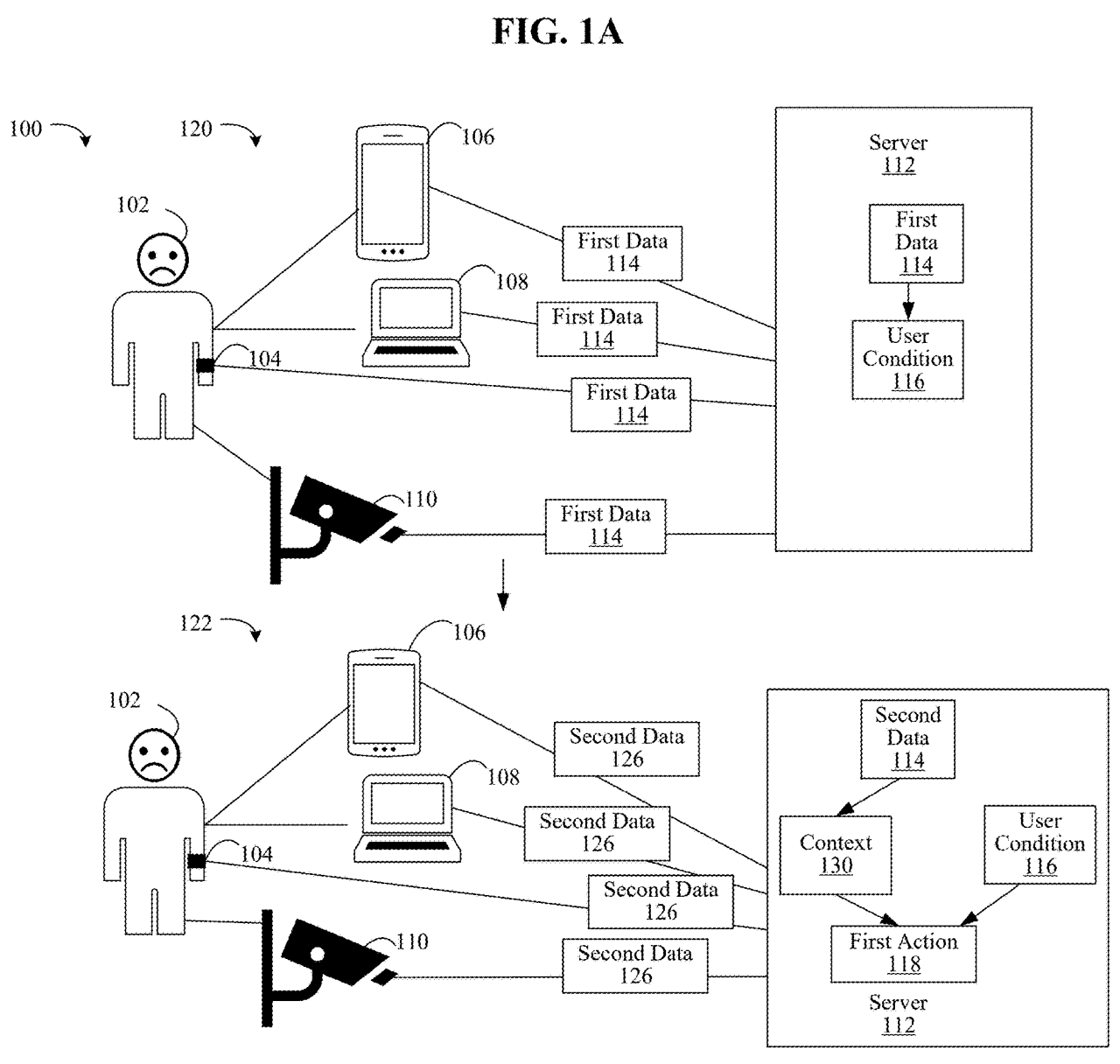

FIGS. 1A-1B is a diagram of an example of a respite process according to an example;

FIG. 3 is a flowchart of an example of establishing baseline measurements according to an example;

FIG. 4 is a flowchart of an example of identifying heart rate variability (HRV) according to an example;

FIG. 11 is a flowchart of an example of taking action to mitigate a user condition based on a context according to an example;

DETAILED DESCRIPTION

Figure 1B:
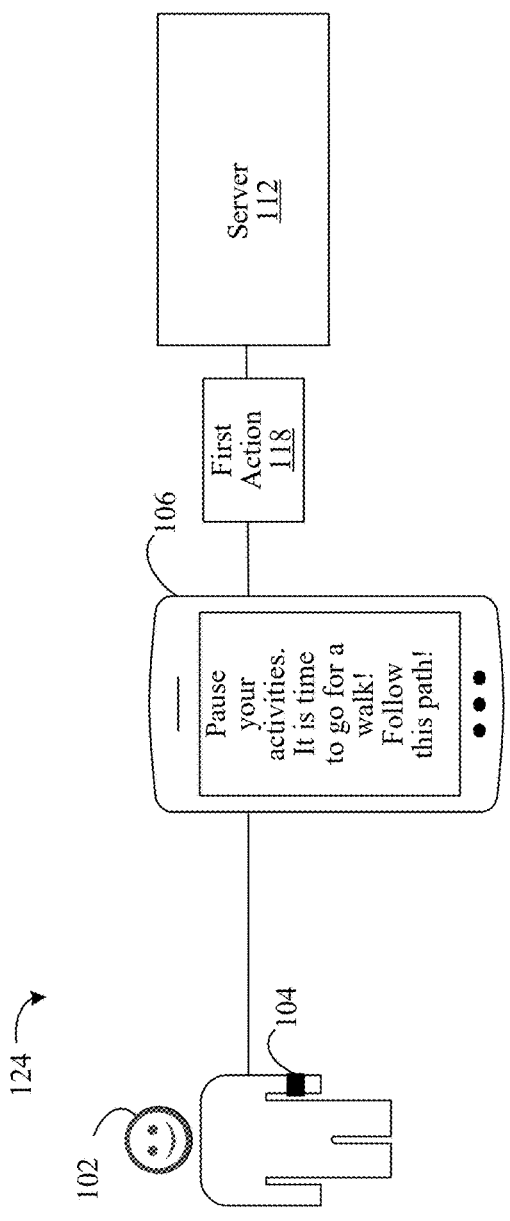

The American Psychological Association (APA) defines anxiety as an emotion characterized by feelings of tension, worried thoughts, and physical changes like increased blood pressure. Individuals with anxiety disorders usually have recurring intrusive thoughts or concerns. They may also have physical symptoms such as sweating, trembling, dizziness or a rapid heartbeat. According to the World Health Organization (WHO), 1 in 13 individuals globally suffer from anxiety. Potential causes have been determined to include environmental stressors, such as difficulties at work, relationship problems, noise, fear etc. A natural tendency is for these individuals to avoid certain situations out of worry.

For example, research has found that mental health problems can result in significant lost productivity and therefore significant economic loss for businesses and the global economy overall. The productivity losses manifest in several ways. Firstly, absenteeism (e.g., people suffering from mental health problems) is more prevalent in people suffering from mental health problems. That is, people with mental health problems utilize a greater number of vacation and/or mental health days in a professional context. Secondly, presentee-ism (e.g., lost productivity that occurs when employees are not fully functioning in the workplace because of an illness, injury, or other condition) is more prevalent in people suffering from mental health problems. Globally and until the year 2030, 12 billion working days will be sacrificed to depression and anxiety every year, which would amount to a cost of more than $900 billion globally. Furthermore, such mental health problems extract a significant toll on personal relationships and personal fulfillment.

Thus, anxiety has grown into a common global phenomenon that affects not only the individuals suffering from negative emotions (e.g., anxiety), but also friends, family and the workplace of such individuals. Identifying, diagnosing and mitigating anxiety is notoriously difficult. For example, a specialist can diagnose a patient based on lengthy conversations and discussions with the patient. Doing so can have several disadvantages, such as human subjectivity, inconsistent application of rules defining the diagnosis of anxiety, patient failure to accurately recall relevant details, biases in diagnosis, etc. Furthermore, doing so can ignore and/or overlook long-term physical manifestations of anxiety, as well as being prone to error. Moreover, such processes are often time-consuming and fail to identify the underlying cause of the anxiety. Furthermore, lengthy processes for which people have to wait to be seen by such specialists (only to be possibly misdiagnosed) are mentally and physically detrimental to the users. Another significant consideration is that the patient may feel uncomfortable speaking with a professional causing many people to forgo treatment. For example, people may need to muster significant resolve and courage to speak with a stranger, who people feel will "judge" them for their feelings or for sharing intimate details of their life.

As a consequence, people can be misdiagnosed. Furthermore, if the underlying cause is not identified and remedied, people can turn to alternative sources to control anxiety, such as medication. Moreover, such manual processes are wildly inaccurate, resulting in an astronomical misdiagnosis rate of 71.0% for generalized anxiety disorder, among other mental disorders. Moreover, many individuals lack access to mental health providers resulting in many individuals failing to ever receive treatment. That is, accurate, timely, accessible, and deeper understanding of the multi-faceted cause of mental health disorders is lacking.

Examples herein provide an automated, accurate, timely efficient and objective process to identify mental health disorders (e.g., anxiety) based on biologically measurable and repeatable factors. Examples identify situations that can lead to the negative emotions associated with the mental health disorders and mitigate the negative emotions. Examples can also intervene when the situations are detected and prior to the negative emotions actually occurring to prevent the negative emotions. Examples increase mindfulness to alleviate the users from anxiety induced state by using customized, proven, preventative measures and 'beacons' for relief. Notably, examples herein can integrate numerous sensory and other data from internet-of-things (IoT) devices to identify when the user has a mental health disorder, identify the underlying cause and remedy the mental health disorder. Examples herein automatically execute and can operate in a completely automatic format to avoid manual intervention.

Indeed, doing so provides several enhancements, including removing bias and subjectivity from the decision making process while reducing the latency to diagnose an individual. Furthermore, examples herein can analyze a user in a deeper and more holistic fashion than existing manual approaches. For example, manual approaches cannot analyze a user's biological signals continuously throughout the course of a day, and fail to accurately identify different causes of the anxiety. Examples herein can receive measurements of the user in real time to quickly ascertain events that cause mental health problems and address the problems in a timely, accurate and meaningful manner. Indeed, examples herein can be accessible to large segments of the population and do not hinge on the availability of human service providers.

Examples identify negative emotions (e.g., anxiety) in a repeatable and reliable manner. The identification process exploits data captured by internet-of-thing devices. For example, wearable devices can capture different biological measurements of a user and accurately provide a clear indication of the user. For example, anxiety can be determined by regularly polling a user's oxygen levels, heart rate variability (HRV) (e.g., the interval between heartbeats), heart rate, etc. with a smartwatch. For example, an unusual mental state can be identified if a patient's heart rate is above 120 beats per minute (BPM) while the user is inactive, or below 40 BPM when the user is not sleeping. Other internet-of-things devices can also detect distinctive characteristics of the user. For example, an imaging device can also detect pupil dilation (increase in dilation indicates anxiety), facial expressions, breathing rates, etc. which corresponds to anxiety. An auditory device (e.g., an artificial intelligence voice assistant) can detect utterances of the user, breathing rate, etc. Thus, numerous different IoT devices can be utilized. A connected car can provide details if the user is driving, in traffic, listening to a certain podcast music, radio station etc. A speaker can provide details as to music (or other audio) that is being generated. A microphone can detect audio in an area surrounding the user. A mobile device can provide details as to whether the user is accessing a certain application on the mobile, texting with another person, executing a particular action on the mobile device, etc. A computing device can provide details as to whether the user is working, on a particular website, etc. A thermostat can provide ambient temperature readings, etc. A continuous glucose monitor can provide glucose readings, where the glucose readings correspond to different mental states.

In order to accomplish the above, examples receive first data and second data from an IoT device associated with a user, where the first data includes a measurement of the user. Examples further determine a user condition based on the received first data, determine a context (e.g., cause of the user condition, trigger, etc.) associated with the user condition based on the received second data, determine a first action to mitigate the user condition based on the context, and provide the first action to a user device associated with the user, where the user device is to execute the first action. Doing so enables the enhancements described above and can occur in a fully automated computing system. Furthermore, doing so mentally would be impossible since continuously monitoring the user by receiving data from IoT devices cannot be performed mentally. Furthermore, it would be impossible to mentally do so with the same level of accuracy and in real-time, and as noted above.

Thus, in some examples, once a user's (e.g., patient) anxiety has been determined, a computer architecture obtains a status "snapshot" of the environment, catalogs the environment and subsequently provides relief which coincides with the user's preferences. This snapshot can encompass physical and digital contexts. The relief could be tailored to counteract the respective environmental trigger (i.e. removal from crowded or noisy environments, avoiding receiving a phone call from a known agitator, bypassing a certain news context etc.). Thus, patients can have heightened awareness of what are typical anxiety triggers for the patient. Some examples aggregate anxiety hotspots for a given individual and/or matching-demographic to proactively alert and avoid/remediate troublesome situations via alternative suggestions or mindfulness therapeutic exercises. Furthermore, some examples aggregate these triggers and associative solutions of the triggers such that the various methods can be quantified and ranked in order of effectiveness (via which have decreased anxiety and/or HRV the most) for both the user as well as those in a shared demographic (e.g., age/sex/location/family status/financial status/employment situation/etc.). Real time feedback can be provided to caretakers and/or users of onset triggers (e.g., context) and also effective calming actions. Examples can also include historical models that can be built to determine which rectifying actions worked best for which triggers (e.g., trained based on a particular user that utilizes the historical model or a population of users that utilize the historical model), thereby providing a more effective measure of respite for the user.

Turning now to FIGS. 1A-1B, a respite process 100 is illustrated. Initially, at first operation 120, a user 102 is monitored with several IoT devices. The IoT devices capture first data 114 of the user 102. The IoT devices include a mobile device 106, a laptop 108, smartwatch 104 and smart camera 110. Other internet-of-things devices can be included, and can include an artificial intelligence voice assistant, a connected car, a speaker, a microphone, a thermostat and/or an imaging device for example.

The first data 114 can correspond to and/or provide sensory data related to an emotional state (e.g., anxiety) of the user 102. For example, the mobile device 106 can capture (e.g., sense) elevated breathing (e.g., via audio readings). The laptop 108 can detect that the user 102 has stopped working (e.g., typing has slowed, no more cursor movements, etc.). The smartwatch 104 can detect that the pulse rate of the user 102 has quickened, and/or that the HRV has little variance, etc. A smart camera 110 can detect that the pupils of the user 102 have dilated. The internet-of-things devices can provide the captured data as the first data 114 to the server 112.

It will be understood that the division of functions between the IoT devices and the server 112 can be flexible. For example, the IoT devices can provide raw sensory data to the server 112. The server 112 can then process the raw sensory data to determine an emotional state of the user 102. In some examples, the IoT devices can provide an analysis (e.g., has a mental health disorder, anxiety, etc.) of the user 102 based on data sensed by the IoT devices.

In this example, the server 112 receives the first data 114 from the IoT devices. The server 112 can then process the first data 114 to determine the emotional state of the user 102. For example, the server 112 can identify a user condition 116 (e.g., a mental health disorder and/or negative emotion) based on the first data 114.

For example, the server 112 can identify the HRV from the first data 114. The HRV is the variability in a time interval between consecutive heartbeats in milliseconds. The heart rate, on the other hand, refers to the number of times a heart beats per a predefined time interval (usually a minute). For example, a heart can beat 60 times per minute. The intervals between heart beats may not be uniformly distributed such that one beat per second. For example, one pair of beats can be 0.8 seconds apart and the next can be 1.20. HRV represents this variation.

As will be explained below, the autonomic nervous system is responsible for controlling cardiac functions. A high heart rate variability is a desirable trait and indicates that the autonomic nervous system is balanced. That is a high HRV can indicate that the user 102 is responsive to different stimuli and is not in an extended state of stress, anxiety etc. On the other hand, having a low heart rate variability can indicate that the user 102 is in an extended state of stress. That is, a low HRV can indicate that a sympathetic system of the nervous system is dominating, and sending stronger signals to the heart of the user 102 than other systems resulting in a low HRV (e.g., heartbeats are consistently spaced apart from one another). Notably, monitoring and identifying the HRV cannot occur mentally, since a computing architecture continuously identifies the heartbeats and HRV. Indeed, identifying the HRV in a manual fashion would be difficult, if not impossible to accurately perform given the small length of time between heart beats and given the minute distinctions in HRV (e.g., milliseconds) that would be imperceptible to a human.

In this example, the server 112 identifies that the user 102 is experiencing a user condition 116 (e.g., negative emotion such as anxiety and/or a mental health disorder). Conventional examples can provide limited guidance after such an identification of a negative emotion relying on outdated and overly broad suggestions. Such conventional examples are ineffective at determining a proper treatment to mitigate the user condition 116. That is, such conventional examples can provide generic guidance to mitigate the user condition 116, which is likely to be ineffective and result in little to no mental change in the user 102.

Turning to operation 122, examples herein provide focused guidance based on previous history and understanding of the user 102. For example, the server 112 can request contextual clues from the IoT devices. In turn, the IoT devices can provide the contextual clues as second data 126 to determine a context 130 (e.g., trigger) of the user 102. The context 130 can facilitate the identification of actions to mitigate the user condition 116.

For example, anxiety and other mental health disorders can be caused by a number of different factors, ranging from negative personal interactions, occupational stresses, financial duress, news, online content, etc. Using a similar approach for each cause would be ineffective. That is, the actions taken to mitigate the user condition 116 can be varied depending on the nature of the cause of the anxiety. Thus, examples consider not only the emotional state of the user

102, but also the underlying cause of the emotional state, encapsulated as the context 130, to determine how to mitigate the user condition 116.

Thus, the server 112 can transmit a request to the IoT devices to provide contextual clues (e.g., audio, video, messaging records, schedule, location, emails, etc.). The contextual clues can be encompassed as the second data 126. The server 112 can identify the context 130 based on the second data 126. The context 130 can indicate a situation of the user 102, such as working, talking to a friend, reading the news, watching TV, in a crowded location, in transit, etc.

The server 112 can generate a first action 118 based on the context 130 and the user condition 116. For example, if the context 130 indicates that the user 102 is working, the first action 118 can include recommending a break, turning off work emails and communications for a predetermined amount of time, meditating, providing distracting games, news, comments to distract the user 102 from work. If the context 130 indicates that the user 102 is speaking to a person, the recommendation can be to recommend that the user 102 to cease communication with the person, block the person from communicating with the mobile device 106 and/or laptop 108, limiting contact with the person, suggesting a break, etc. As such, the server 112 can generate focused guidance to address the user condition 116 based on the context 130.

Turning now to FIG. 1B, at operation 124, the server 112 can provide the first action 118 to the mobile device 106. The first action 118 can cause the mobile device 106 to present a calming message. As illustrated the message can calm the user 102. In some examples, the server 112 can continue to monitor the user 102 to determine whether the user condition 116 is mitigated. If not, the server 112 can provide further actions to the mobile device 106 to calm the user 102.

Figure 2A:
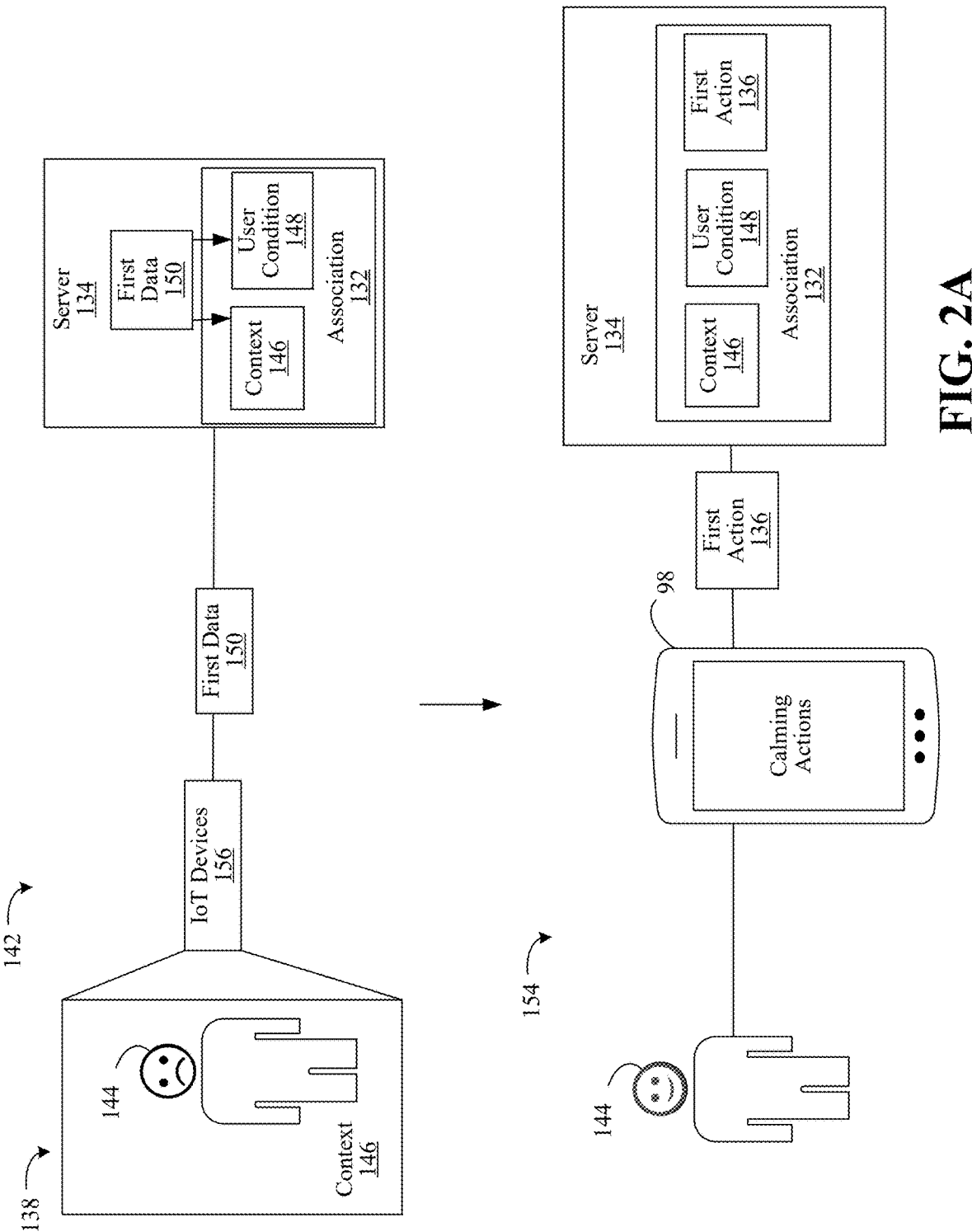
FIGS. 2A-2B is a diagram of an example of a context identification and mental state remediation process according to an example.
Figure 2B:
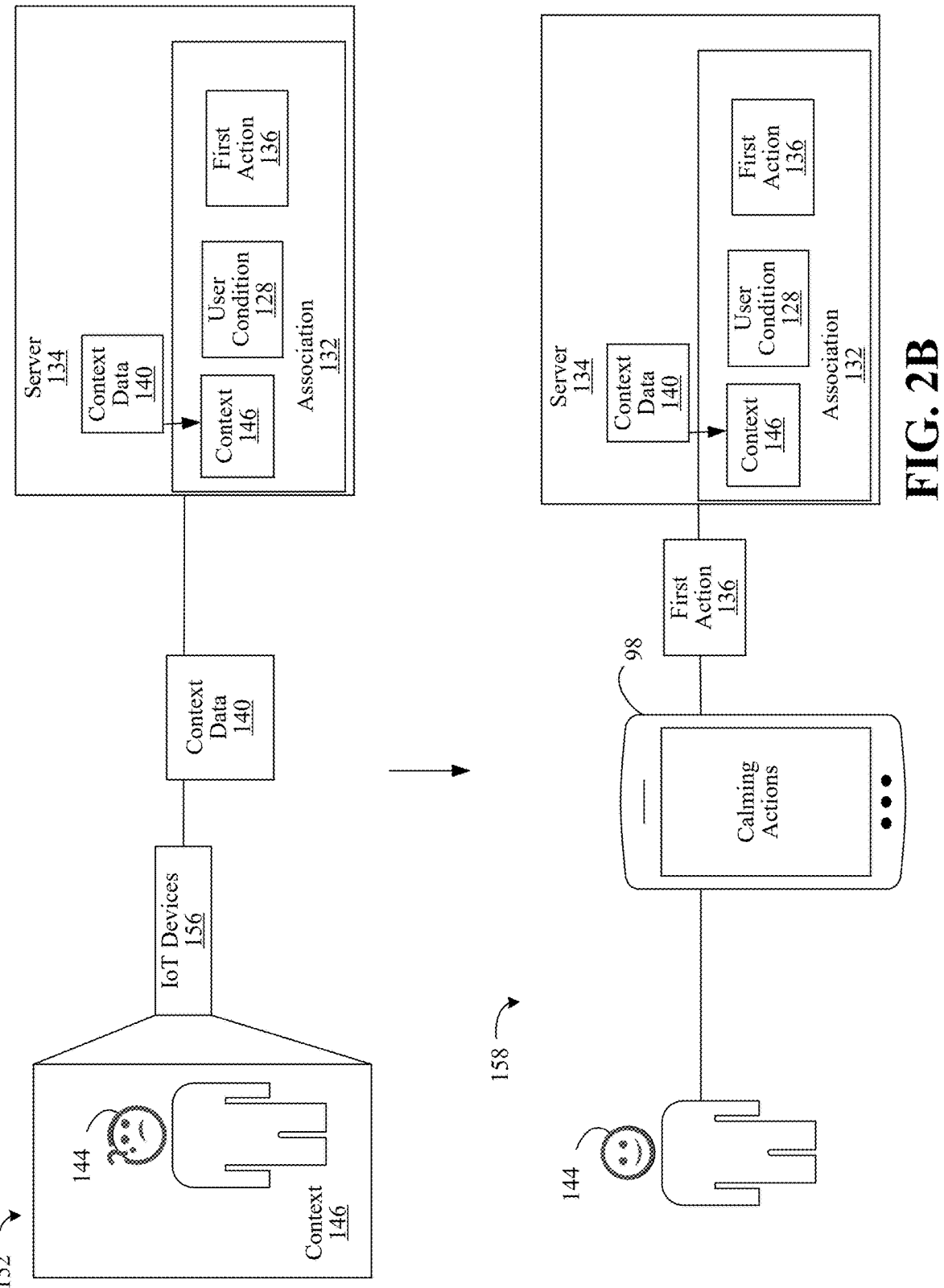

FIGS. 2A-2B illustrate a context identification and mental state remediation process 138. The context identification and mental state remediation process 138 can be implemented in conjunction with any of the examples described herein, for example the respite process 100 (FIGS. 1A-1B). In detail, distinct types of context can have different effects on the user. A context can refer to any situation or circumstance that forms the setting for an event, statement, or idea that has a negative effect on the mental health of the user 142, and in terms of which the mental health can be fully understood and assessed.

Thus, examples seek to not only understand when a user 142 is experiencing a mental health disorder (e.g., negative emotion) and address the mental health disorder, examples seek to also understand the underlying cause (e.g., context) that results in the mental health disorder. In doing so, examples can actively stop some negative emotions from ever occurring.

Doing so presents unique challenges. For example, in some cases accessing and identifying relevant information in real-time can be an overwhelming task. For example, a human being would be prone to biases, errors and mis-identification due to the complicated nature of human emotions. Humans employ a subjective process to identify emotions, and the cause of the emotions. In many cases, the subjective process is heavily biased by the humans' experiences, education and limited observations. Furthermore, identification of the emotions can rely on a limited dataset (e.g., visual observations and conversation). Moreover, the cause of the emotions may go unnoticed. For example, identification of the cause of emotions can be an overwhelmingly complex process that extends over numerous days, hours and weeks. Indeed, in many cases humans themselves cannot piece together the cause of the negative emotions, and rely only on what the humans can recall. Relying on human memory alone is prone to error since humans cannot accurately recall all details.

Examples as described herein remedy the above by implementing a rigorous, objective process to identify human emotion, and the cause of the human emotion. That is, examples can readily identify the cause of human emotions by careful and thorough observation harvesting and analysis that can occur in real time and continuously. Example can execute in real time to readily and expediently identify the cause of different emotions and remedy the emotions.

It is worth noting that the mobile device 106, laptop 108, smartwatch 104, smart camera 110 and server 112 can communicate over a network(s). The network(s) can include, or operate in conjunction with, an ad hoc network, an intranet, an extranet, a virtual private network (VPN), a local area network (LAN), a wireless network, a low energy Bluetooth (BLE) connection, a WiFi direct connection, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network can include a wireless or cellular network and the coupling can be a Code Division Multiple Access (CDMA) connection, a Global System for Mobile communications (GSM) connection, or other type of cellular or wireless coupling. In this example, the coupling can implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, fifth generation wireless (5G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

For example, turning now to FIG. 2A, the process 138 identifies a context 146 is illustrated. In this example, IoT devices 156 can observe the user 144. The IoT devices 156 can provide first data 150 to the server 134 in real-time. The first data 150 can be a constant stream of data associated with the user 144. The IoT devices 156 can include mobile devices, smartwatches, computing devices, thermostats, televisions, etc. Notably, the first data 150 can include data that is observed over a number of days, hours, minutes, seconds, etc. and is provided in real time to the server 134. The server 134 can analyze the first data 150 to determine the context 146 and the user condition 148. The server 134 can store the context 146 in association with the user condition 148.

For example, the user condition 148 can be a negative emotion (e.g., anxiety) that is determined from the first data 150. The server 134 can identify the cause of the user condition 148 based on the first data 150. For example, the server 134 can determine the events that occurred prior to the user condition 148 being identified. The server 134 can analyze all events for a predetermined timeframe preceding the time that the user condition 148 was identified. The events can be detected from the first data 150 (e.g., a continuous stream of data).

For example, initially the server 134 can identify and transcribe all events in a predetermined amount of time prior to the user condition 148 being detected. Notably, the user condition 148 can be repeatedly identified at different times (e.g., hours apart, days apart, etc.) Each time that the user condition 148 is detected (e.g., on separate occasions), the events leading up to the user condition 148 can be recorded. The server 134 can then compare the events that are recorded each time the user condition 148 is detected to identify the common events that occur prior to the user condition 148 being detected. Doing so provides several enhancements, such as accurate detection of causes of the user condition 148 and mitigation strategies focused and customized for the particular situation of the user 144. The events can be part of the context 146.

As another example, people can have a faulty understanding of stressors. For example, people can overlook the notion that seemingly innocuous events can actually be stressful in combination with other events or individually. For example, some people can have subtle reactions to the news. Although the people do not necessarily have an immediate reaction to the news, the people can react several hours later upon further reflection and contemplation on the news. Similarly, people can have reactions to personal conversations after the conversations have completed. Examples herein track the events of the user 144 over a period of time to fully understand how the user reacts to daily events, even when emotional responses are temporally separated from the events.

In some examples, when an event is detected a certain amount of times in the time prior to the user condition 148 being detected such that the amount of times meets a threshold, the event can be stored as the context 146 and in association with the user condition 148. In some examples, the first data 150 can include scheduling information (e.g., from an electronic calendar), health records, mental health evaluations, social network details, etc. For example, the schedule can be analyzed to determine whether a particular event (e.g., meeting with a supervisor) is consistently identified (e.g., number of times the particular event is detected prior to the user condition 148 meets the predetermined threshold) in association with the user condition 148, and stored as the context 146 if so.

Thus, some examples are not limited to reactive measures alone. By analyzing historical triggers and associated action mappings, examples can further aid in the determination and avoidance of future triggers for patients who fit into the user's demographic. Detection of future anxiety inducing events can be provided via the analysis of the user's electronic calendar to determine if there are meetings, places, routes, or activities which have historically created an anxiety inducing event. Preemptive calming can be provided by introducing calming measures and anxiety reducing techniques which have historically helped the individual and their associated demographic-including exercises, music, location recommendations, alternative routes, humorous articles prior, etc. to calm the user 144, etc. Thus, the actions, such as first action 136, can be pre-emptively provided to the user 144.

The server 134 and IoT devices 156 can leverage readily available sensors found in wearables today to search for potential environmental triggers of anxiety including but not limited to location, sound, and a number of people present and nearby the user 144. The number of people can be estimated via location data retrieved from other user devices and/or social media. Application programming interfaces (APIs) can readily be available for such a purpose (e.g., busy time forecasts API and foot traffic forecasts API). For example, an API can identify anonymous phone signals to obtain a people count. Other factors that can be analyzed include the speed at which the individual is moving, whether an event is occurring at that user's location, geo-spatial context, typical business area details that the user 144 can be located within (e.g., shopping of the area, foot traffic), topological features (e.g., water nearby, climate, elevation, etc.) and frequency of user experiencing anxiety in a particular physical space.

Some examples can further extend to environmental contexts (e.g., triggers) that can be extended to the logical and/or mental landscape. These types of triggers include applications as well as specific application features, news article, websites, streaming application content (e.g., videos) and so forth. Further delineation can be made at an application level or the subjects and/or topics from which of the consumed content. Specific themes can also be identified that extend throughout the contexts listed above. For example, new articles and social media posts whose primary topic is student loans (e.g., the context can include student loan information). Music applications can also be another trigger.

Some examples can identify anxiety bubbles. An anxiety bubble is a physical places or logical entity which have proven to be anxiety inducing to the user 144 as well as a shared demographic. Logical entities can extend to the following. Topics on news applications can be an anxiety bubble. Social media conversational themes can be an anxiety bubble. Specific applications can be an anxiety bubble. Types of contacts (e.g., work related) can be an anxiety bubble. Specific contacts (e.g., ex-spouse) can be an anxiety bubble. These anxiety bubbles can be historically proven to be avoided from which we "predict' and quantify anxiety hotspots to avoid.

The server 134 will be able to guide the user to a personalized environment for relief. The environment may be a physical location (e.g., a different physical location) or a mental location (e.g., by adjusting the headspace via comforting actions, application usage, etc.). Doing so provides personalized relief that is determined via a preregistration stage where the client would undergo an initialization process (explained below).

In some examples, during a training phase, the server 134 can be trained to identify suitable actions to mitigate different conditions. An aggregation of calming mechanisms across all users of the respite systems can be used to provide more robust benefits across a community of users. The aggregated remedying "solutions" can be quantified and ranked in order of effectiveness (via which actions have decreased HRV the most) for both the individual as well as those in the shared demographic (e.g., age/sex/location/ family status/financial status/employment situation/etc.). Doing so can lead to more robust recommendations in the training phase as well as the respite phase. Furthermore, some examples can predict and quantify anxiety inducing location based hotspots to avoid based on demographic information.

After the completion of this training process, examples can then help the user 144 experience an environment which fits with a calming profile of the user 144 at times of determined anxiety. The assistance to unite the anxious user with a calming environment can include but not be limited to:

1) Navigating to a quiet space/location which fits a calming profile of the user 144 (e.g., a coffee shop, hiking area, restaurant, etc.). This can be enhanced by avoiding certain places that have historically been triggers and/or popular trigger scenarios from those in a demographic of the user 144.
2) Playing relaxing sounds (e.g., preregistered artists or music), and/or suggest listening to certain types of audio (e.g., comedic podcasts).
3) Blocking communication (e.g., calls/texts) from anxiety inducing individuals or entities.
4) Providing suggestions for communication with a calming individual/entity (e.g., calling mother, therapist, father, etc.).
5) Providing options based on persons availability, such as walk, stand, stretch, depending on their willingness/ time allotment (assessed via electronic calendar integration).

Thus, in some examples an electronic calendar can be accessed to identify time constraints of the user 144, and determine an appropriate action that meets the time constraints (e.g., fits within a free time period). As noted, prior, the effectiveness of the recommendations can be analyzed via a significant HRV increase as well as by soliciting the user with a survey of effectiveness such that future participants training phases can leverage this feedback for more confident suggestions via demographic aggregation. As such, the server 134 can include a machine learning component to learn different actions, contexts and user conditions.

The notion of respite is not limited to reactive measures alone. By analyzing historical triggers and associated solution mappings, examples further aid in the determination and avoidance of future triggers for those who fit into the demographic of the user 144. Detection of future anxiety inducing events can be provided via an analysis the user's 144 electronic calendar to determine if there are meetings, places, routes, or activities which have historically created an anxiety inducing event. Preemptive calming can be provided by introducing calming measures and anxiety reducing techniques which have historically helped the user 144 and associated demographic of the user 144, such as exercises, music, location recommendations, alternative routes, humorous articles prior, etc. to calm the user 144.

During the registration process, examples can define what the user 144 finds calming. Examples can analyze the biometrics of the user 144, such as HRV, to verify what the user finds calming. Examples can also identify triggers for population (e.g., demographics) and have pockets to avoid or to recommend. Demographics can include employment levels, marital status, race, family, etc. Examples can also analyze location and sound to identify what can be implemented in an IoT fashion, Tik-Tok, twitter, etc. triggers. Some examples can recommend exercise etc. to pre-emptively buffer stressful events. Some examples can provide external stimuli that the user 144 has not yet experienced and based on the actions that were proven effective for a demographic group of the user 144. Examples can also inquire to the user 144 and request that the user 144 provide details as to what calmed the user 144, and additionally expose the user 144 to new stress methods.

Once the user's 144 anxiety has been determined, the process 138 obtains a status 'snapshot' of the environment, catalogs the environment as the context 146 and subsequently provides relief which coincides with the preferences of the user 144. The relief can be tailored to counteract an environmental trigger (e.g., removal from crowded or noisy environments, avoid providing a phone call from a known agitator, etc.). Some examples provide patients with awareness of typical anxiety triggers that are identified for the patients. The aggregation of anxiety hotspots for a given individual and/or matching-demographic to proactively alert and avoid and/or remediate troublesome situations via alternative suggestions or mindfulness therapeutic exercises.

Examples can aggregate these triggers (can be adjusted based on the type of trigger and a classification of the trigger) and associative actions. Various methods can be quantified and ranked in order of effectiveness (e.g., which methods have decreased HRV the most) for both the individual as well as those in a shared demographic (e.g., age, sex, location, family status, financial status, employment situation, etc.).

At operation 154, the server 134 can provide a first action 136 to a user device 98. The first action 136 can be identified based on a historical record of actions that calmed the user, and/or a historical record of actions that calmed a demographic group of the user 144 as noted above. The first action 136 can be a list of calming suggestions and/or automatic implementations to mitigate the user condition 148 as identified based on a ranking of actions that increased HRV.

For example, the first action 136 can be an action to automatically block an application on the user device 98. For example, if the context 146 indicates that the application (e.g., social media application, work related application, news application, messaging, banking application etc.) is the cause of the user condition 148, the application can be automatically blocked (e.g., rendered inaccessible, stopped from executing, block the application from executing a task) for a predetermined amount of time and the user 144 can be notified of the block of the application.

In some examples, the user 144 is notified of the context 146 (e.g., trigger for negative emotions), and third-parties (e.g., guardians, parents, teachers, therapist, medical professionals, etc.) can also be notified. The first action 136 can also be an instruction and/or suggestion for the user 144 to perform an action (e.g., take a break, meditate, work out, breathe deeply, etc.) to create a calming effect.

In some examples, the user 144 can receive a summary of reactive as well as proactive respite actions as well as any applicable caretakers. Doing so allows both parties to gain valuable insight into the specific respite feedback that works for the user 144, in addition to orders of effectiveness of the respite actions. This can be kept for reflective purposes, medical follow ups, etc. The feedback can be extended to real-time notifications of anxiety notifications, identification of the context 146 (e.g., trigger) (and an associated snapshot), and respective respite actions that can be helpful. For example if a child's trigger is an educator, then the parents can be notified to request a change (something a child will not have the leverage to do on their own). This can lead to early intervention of a potential stressful event for those who may not be able to take action for themselves.

An association 132 can be created to store the relationship between the context 146, user condition 148 and first action 136. The first action 136 can also be stored in the association 132 to be associated with the context 146 and the user condition 148. For example, different users can respond differently to different actions. For example, a first user can have an adverse reaction to a particular action (e.g., the first user experiences greater anxiety when the particular action occurs) rather than having a positive reaction (e.g., calming effect) to the particular action. Rather than providing generic guidance to users, examples herein identify and store actions that are shown or identified to be effective for the particular user.

For example, the user 144 can answer questions in a questionnaire, and actions can be identified based on the answers. In examples, demographics of the user 144 are identified. Actions that were identified to be effective for the demographic are provided to the user 144. After the first action 136 is shown to counteract the user condition 148 (e.g., the HRV increases to be above a threshold), the first action 136 can be stored in the association 132. Thus, when the context 146 and/or user condition 148 are detected, the first action 136 can be automatically provided to the user device 98 since the first action 136 is shown to be an effective treatment.

In some examples, actions can each be quantified into a multi-dimensional vector. The vectors can be mapped to a latent space. Vectors that are close to one another in the latent space represent actions that are similar to each other. Examples can therefore identify effective actions based on previous actions that had a mitigating effect on the user 144 and/or a demographic of the user 144. For example, suppose that the first action 136 is deemed effective for the user 142. In such an example, the first action 136 can be mapped to the latent space, and vectors that are within a proximity to the first action 136 can also be suggested to the user 142 when the user condition 148 and/or context 146 are detected. The vectors can represent different actions that are identified based on the vectors.

In some examples, the server 134 can vectorize the actions (in the first format) to generate vectorized data (e.g., in the second format) that is efficiently processed. The vectorized data can be N-dimensional and can contain vectors representing various actions. Data can be stored in a columnar format (e.g., all values of a column are stored as a single record). Given the larger footprint of potential data, storing data in a columnar format provides several benefits. Such benefits would range from efficient utilization of bandwidth throughout the storage hierarchy via the use of more efficient compression due to the data all being of the same type to speeding up data processing for highly efficient analytical queries. Given that these queries on this data are more analytical in nature it would be beneficial to fit for vectorized processing. In some examples, the server 134 can modify the actions in the first format, to a second data format that is a column-oriented data file format designed for efficient data storage and retrieval.

Turning now to operation 152, at a time after the association 132 between the user condition 128, the context 146 and the first action 136 is generated, the server 134 can receive context data 140 from the IoT devices 156. The server 134 identifies that the context 146 has re-occurred based on the context data 140 received from the IoT devices 156. That is, the server 134 detects that the context 146 can lead to the user condition 128 based on the association 132, and therefore mitigation efforts should be executed. That is, the server 134 accesses the association 132 (e.g., a past record of the user), identifies a previous action(s) that mitigated a previous condition(s) associated with the user based on the past record, and selects the first action 136 based on the previous actions and the user condition. Thus, examples can also receive context data (e.g., third data) from the IoT devices 156, identify the context 146 from the context data 140, determine that a probability of the user condition 128 occurring in the future is above a threshold based on the context 146 being identified from the context data 140, identify a first action 136 and/or a second action to mitigate the user condition 128 and based on the probability of the user condition occurring in the future being above the threshold.

The context 146 has not yet led to the user condition 128 being observed in the user 144. That is, the user 144 does not yet have the user condition 128. Based on the association between the context 146 and the user condition 128, the server 134 can determine that it is likely (e.g., a probability of the user condition 128 occurring is above a threshold) that the user condition 128 will develop since the context 146 is identified.

The server 134 can then take preemptive actions at operation 158. For example, at operation 158 the server 134 can provide the first action 136 to the user device 98, similar to as described in operation 154. For example, the first action 136 can calm the user 144 and is transmitted based on the first action 136 being associated with the context 146. The user 144 can then be pre-emptively calmed prior to the context 146 generating the user condition 128 in the user 144. In some examples, multiple actions can be executed based on the latent space analysis of vectors described above.

It is worth noting that the IoT devices 156 and server 134 can communicate over a network(s). The network(s) can include, or operate in conjunction with, an ad hoc network, an intranet, an extranet, a virtual private network (VPN), a local area network (LAN), a wireless network, a low energy Bluetooth (BLE) connection, a WiFi direct connection, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network can include a wireless or cellular network and the coupling can be a Code Division Multiple Access (CDMA) connection, a Global System for Mobile communications (GSM) connection, or other type of cellular or wireless coupling. In this example, the coupling can implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, fifth generation wireless (5G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

FIG. 3 illustrates a method 250 of establishing baseline measurements of a user. The method 250 can be implemented in conjunction with any of the examples described herein, for example respite process 100 (FIGS. 1A-1B) and context identification and mental state remediation process 138 (FIGS. 2A-2B). In an example, the method 250 is implemented in logic instructions (e.g., software), configurable logic, fixed-functionality hardware logic, computer readable instructions stored on at least one non-transitory computer readable storage medium that are executable to implement method 250, circuitry, etc., or any combination thereof.

Illustrated processing block 252 monitors a user over a predetermined amount of time. Illustrated processing block 254 establishes normal parameters of the user. That is, each user can have different biological metrics (e.g., heart rate variability, pulse, heart rate, etc.). Thus, illustrated processing block 256 defines the average and standard deviation for the parameters. The average and standard deviation for the parameters can be the baseline. In some examples, the parameters include heartbeat, HRV, breathing rate, pupil dilation, temperature, etc. Illustrated processing block 258 compares future user readings to the average and standard deviation for the parameters to determine when the user readings are anomalous and deviate from a resting (normal) situation. In such instances, the user can be identified as having a mental disorder (e.g., anxiety attack).

FIG. 4 illustrates a method 270 of identifying HRV. The method 270 can be implemented in conjunction with any of the examples described herein, for example respite process 100 (FIGS. 1A-1B), context identification and mental state remediation process 138 (FIGS. 2A-2B) and method 250 (FIG. 3). In an example, the method 250 is implemented in logic instructions (e.g., software), configurable logic, fixed-functionality hardware logic, computer readable instructions stored on at least one non-transitory computer readable storage medium that are executable to implement method 270, circuitry, etc., or any combination thereof.

Illustrated processing block 272 sets a threshold based on a historical record of heart rate variability (HRV) of the user. The historical record can be tracked over a period of several days to week to obtain an accurate understanding of the user's HRV. As noted above, if a user does not have anxiety, the HRV is greater. If the user does have anxiety, the HRV is lower. The threshold can be generated based on the user's average HRV (e.g., a certain percentage lower than the average HRV).

Illustrated processing block 274 measures the HRV of the user. Illustrated processing block 276 identifies that the HRV is below the threshold. Illustrated processing block 278 determines that the user has the user condition (e.g., anxiety) based on the HRV dropping below the threshold (e.g., HRV is lower than expected).

Figure 5:
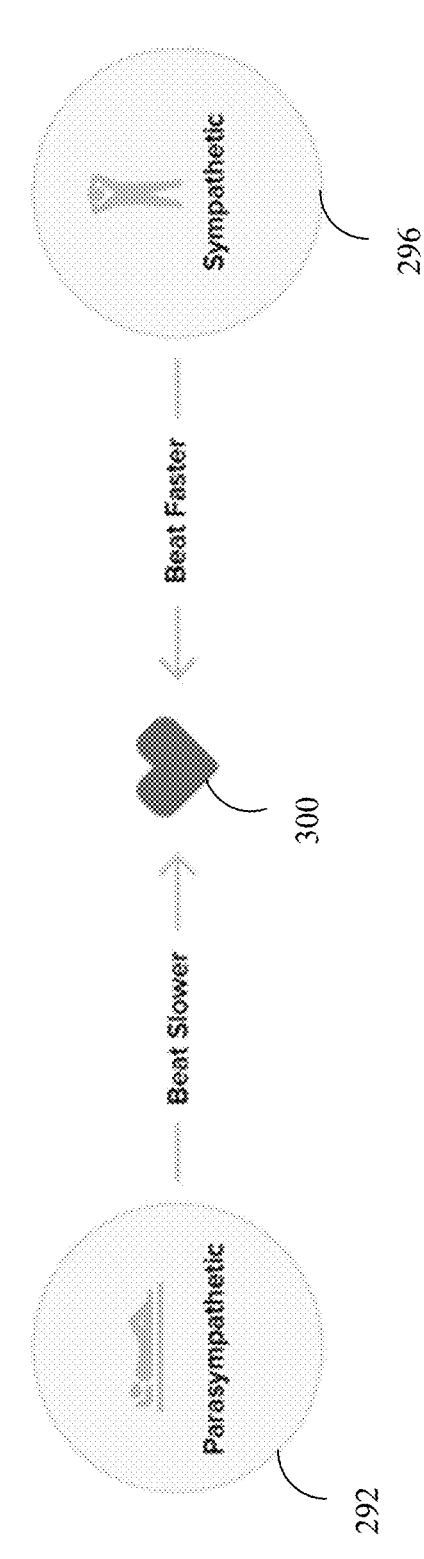
FIG. 5 is a diagram of an example of a diagram of an autonomic nervous system according to an example.

Turning now to FIG. 5, an autonomic nervous system (ANS) diagram 290 is described. The ANS diagram 290 can be implemented in conjunction with any of the examples described herein, for example respite process 100 (FIGS. 1A-1B), context identification and mental state remediation process 138 (FIGS. 2A-2B), method 250 (FIG. 3), and method 270 (FIG. 4). The ANS is required for cardiac function (e.g., heart rate, blood pressure, etc.), respiration, and other reflexes, including vomiting, digestion, coughing, and sneezing. The ANS includes two anatomically distinct portions: the sympathetic nervous system 296 (e.g., activates the fight or flight response) and parasympathetic nervous system 292 (e.g., deactivates and initiates the rest/recover response). The sympathetic nervous system 296 thus controls "fight or flight" which in turn burns energy. The sympathetic nervous system 296 does exert a cost, and detrimentally promotes inflammation. If the sympathetic nervous system 296 remains dominant for an extended duration of time, detrimental (e.g., can cause long term health issues such as high blood pressure, digestive track problems, etc.) effects can occur. For example, the sympathetic nervous system 296 can increase heart rate, raise blood pressure, divert blood flow to muscles, drive sugar and/or fat into bloodstream, inhibit digestion, reduce appetite and dilate the pupils. Any of these factors can be identified and analyzed to determine if the sympathetic nervous system is active, and indicates that a user is experiencing a user condition (e.g., anxiety).

The parasympathetic nervous system 292 permits rest and recovery, and can cause energy to be stored as well as be responsible for inflammation suppression. The parasympathetic nervous system 292 also slows the heart rate, decreases blood pressure, dilates blood vessels, promotes energy storage, stimulates digestion increases appetite, and turns up protein synthesis.

As the sympathetic nervous system 296 activates, the heart 300 beats execute closer together, or beats faster 298, and the time between heart beats shortens. The opposite occurs with the parasympathetic nervous system 292. That is, for the parasympathetic nervous system the heart beats slower 294 lengthening the time between beats. Therefore, if a nervous system is balanced, the heart 300 is constantly being told to beat slower by the parasympathetic nervous system 292 and beat faster by the sympathetic nervous system 296. Doing so causes a fluctuation in heart rate and can be quantified via HRV.

Having a high HRV is a desirable trait. Having a high HRV can indicate that a person is responsive to both sets of inputs (e.g., parasympathetic and sympathetic actions). A high HRV can correspond to a nervous system being balanced, and that the body is adaptable to environmental concerns. On the other hand, having a low HRV indicates that one branch is dominating, usually the sympathetic nervous system 296. The sympathetic nervous system 296 sends stronger signals to the heart 300 than the parasympathetic nervous system 292. In some cases, such a scenario is natural and normal, such as if a person is running a race, the person wants the body to focus on allocating resources to the legs (e.g., sympathetic activity) as opposed to maintenance activities like digesting food (e.g., parasympathetic activity).

If a person is not participating in a physical activity, then having a low HRV can indicate that the person's body is active for some other reasons (e.g., fatigued, dehydrated, stressed, sick and need to recover, etc.), which leaves fewer resources available to dedicate towards other activities such as exercising, providing a presentation at work, body maintenance tasks, etc. Such a situation not only affects traditional physical tasks, but also mental well-being in intellectually demanding situations (e.g., occupational work, school, etc.). While productivity gains may be made in the short term for a busy season; over time, stress can lead to health problems such a high blood pressure, mental health problems like depression and anxiety, and burnout which lead to employees missing work or leaving a job entirely. Examples herein leverage HRV analysis to determine when a user has low HRV, and correspondingly is in a state of anxiety and/or stress.

Figure 6:
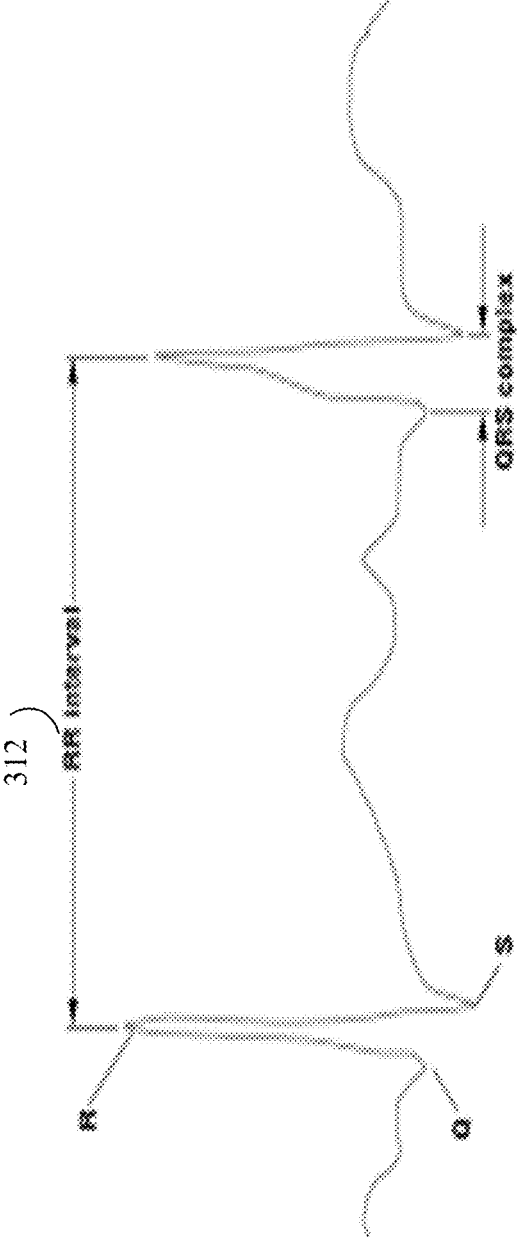
FIG. 6 is a diagram of an example of an HRV electrocardiogram according to an example.

Turning now to FIG. 6, an HRV electrocardiogram 310 is illustrated to describe how to measure HRV. The HRV electrocardiogram 310 can be implemented in conjunction with any of the examples described herein, for example respite process 100 (FIGS. 1A-1B), context identification and mental state remediation process 138 (FIGS. 2A-2B), method 250 (FIG. 3), method 270 (FIG. 4) and ANS diagram 290 (FIG. 5). There are several time-domain indices of HRV electrocardiogram 310 used to quantify the amount of variability in measurements of the interbeat interval (IBI), which is the time between successive heartbeats, see Table I below:

TABLE I

| NAME | UNIT OF MEASUREMENT | DEFINITION |
|---|---|---|
| SDNN | ms | Standard deviation of NN intervals or time interval between R peaks. R peaks can be a maximum amplitude in the R wave. NN interval can be another way of saying "normal"/artifact-free RR interval. The letter N is used to distinguish that these statistics are intended to derive from "normal" RR intervals, or RR intervals which represent normal cardiac timing and are free from artifacts which can occur in normal RR readings. Whereas regular RR intervals are intervals between successive heartbeats as the successive heartbeats occur. |
| SDRR | ms | Standard deviation of RR intervals, where RR intervals are the time elapsed between two successive R waves. |
| SDANN | ms | Standard deviation of the average NN intervals for each 5 min segment of a 24 hour HRV recording, where an NN interval is the Time (normalized) between two detected heartbeat detections. |
| SDNN index (SDNNI) | ms | Mean of the standard deviations of all the NN intervals for each 5 min segment of a 24 hour HRV recording |
| pNN50 | % | Percentage of successive RR intervals that differ by more than 50 ms |
| HR Max - HR Min | bpm | Average difference between the highest and lowest heart rates during each respiratory cycle |
| RMSSD | ms | Root mean square of successive RR interval differences |
| HRV triangular index | | Integral of the density of the RR interval histogram divided by its height |
| TINN | ms | Baseline width of the RR interval histogram |

Examples herein can analyze HRV based on a Root Mean Square of Successive Differences (RMSSD). This is the RMSSD between each heartbeat. The RMSSD is relatively simple to calculate to reduce processing overhead for large-scale computations and provides a reliable measure of HRV and parasympathetic activity. Examples rely on the RR interval 312, which is defined as the peaks of the heartbeat as shown in FIG. 6.

The QRS complex can be a combination of three of the graphical deflections seen on an electrocardiogram (ECG or EKG). The QRS complex is usually the central and a visually noticeable portion of the tracing. The QRS complex corresponds to the depolarization of the right and left ventricles of the heart and contraction of the large ventricular muscles.

In adults, the QRS complex normally lasts 80 to 100 ms; in children the QRS complex may be shorter. The Q, R, and S waves occur in rapid succession, do not all appear in all leads, and reflect a single event and thus are usually considered together. A Q wave is any downward deflection immediately following the P wave. An R wave follows as an upward deflection, and the S wave is any downward deflection after the R wave. The T wave follows the S wave, and in some cases, an additional U wave follows the T wave. The QRS complex may be provided for completion to display other phenomena in a ECG/EKG image. The RR intervals may further be relied on.

Figure 7:
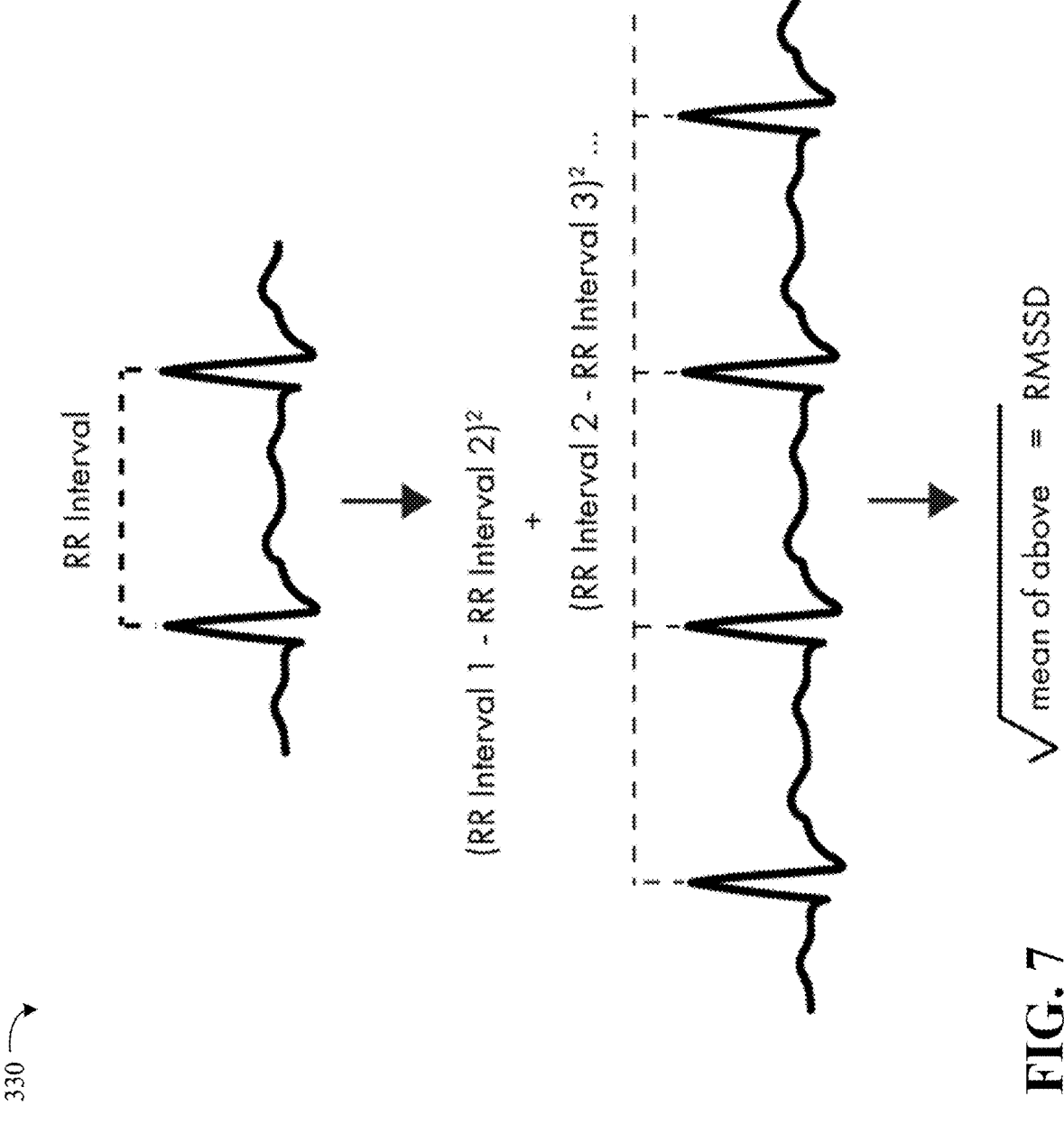
FIG. 7 is a diagram of an example of a HRV calculation process according to an example.

Turning now to FIG. 7, an RMSSD calculation process 330 to calculate the RMSSD is illustrated. The RMSSD calculation process 330 can generally be implemented in conjunction with any of the examples described herein, for example respite process 100 (FIGS. 1A-1B), context identification and mental state remediation process 138 (FIGS. 2A-2B), method 250 (FIG. 3), method 270 (FIG. 4), ANS diagram 290 (FIG. 5) and electrocardiogram 310 (FIG. 6). In this example, the following equation identifies the RMSSD of two beats:

$$\sqrt{(RR \text{ interval } 1 - RR \text{ interval } 2)^2} \qquad \text{Equation 1}$$

The following equation can be followed for multiple heart beats (greater than two):

$$\text{Equation 2}$$

$$\sqrt{\begin{array}{l}(RR \text{ interval } 1 - RR \text{ interval } 2)^2 + \\ (RR \text{ interval } 2 - RR \text{ interval } 3)^2 \ldots + \\ (RR \text{ interval } (n-1) - RR \text{ interval } n))^2\end{array}}$$

In order to leverage HRV, some examples obtain an individualized baseline by taking the HRV reading at a same time every day, while the user is not moving (e.g., idleness for a predetermined amount of time, such as 180 seconds), at the same body position each day in order standardize the assessment. Examples employ the RMSSD analysis above to establish this baseline for our patients and use relative jumps in the HRV rate to establish moments of anxiety.

Significant drops occur in HRV when a stressor is introduced, thereby, showing a lower variation rate once a stressor occurs as compared to baseline. Different groups (e.g., those with generalized anxiety disorder and those without generalized anxiety) showed significantly lower HRV during moments of anxiety as compared to the resting condition.

Examples leverage this phenomenon to take consistent HRV measurements (once every X seconds—where X can be measured to optimal testing, such as 200 seconds) at times of idleness (idleness can be classified by restricted movement of duration Y seconds—where Y can be measured to optimal testing such as 180 seconds) to search for times of patient anxiety. At these times of anxiety, examples will seek to aid the user via customized mitigation tactics dependent on the user's environment and pre-evaluated calming preferences as described above.

Figure 8:
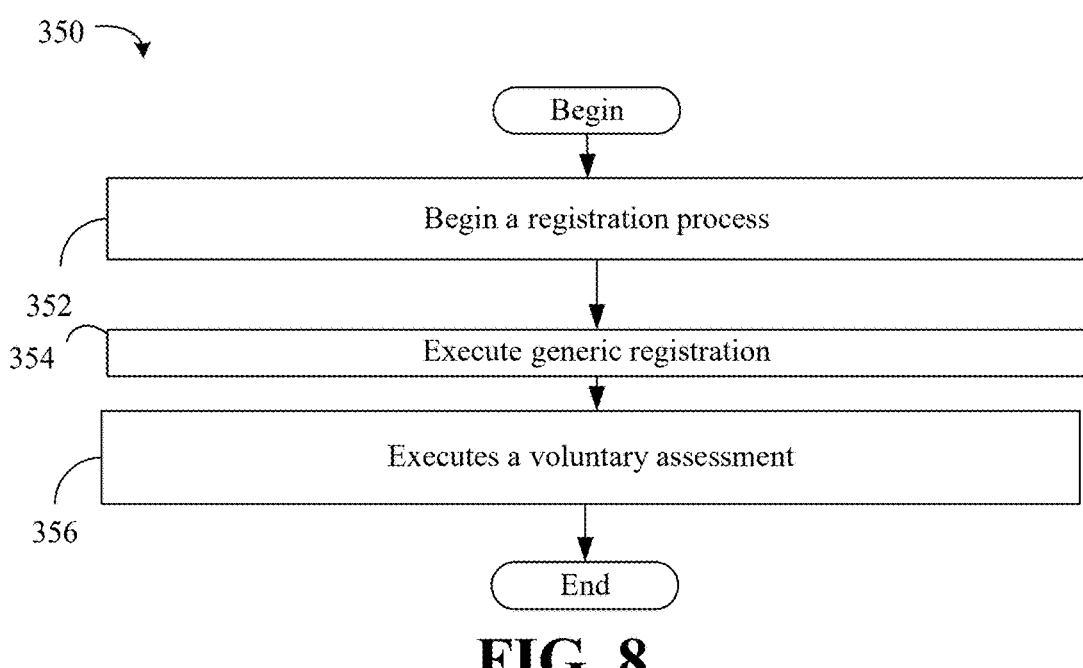
FIG. 8 is a flowchart of an example of registering a user according to an example.

FIG. 8 illustrates a method 350 of registering a user. The method 350 can generally be implemented in conjunction with any of the examples described herein, for example respite process 100 (FIGS. 1A-1B), context identification and mental state remediation process 138 (FIGS. 2A-2B), method 250 (FIG. 3), and method 270 (FIG. 4), ANS diagram 290 (FIG. 5), HRV electrocardiogram 310 (FIG. 6) and RMSSD calculation process 330 (FIG. 7). In an example, the method 250 is implemented in logic instructions (e.g., software), configurable logic, fixed-functionality hardware logic, computer readable instructions stored on at least one non-transitory computer readable storage medium that are executable to implement method 350, circuitry, etc., or any combination thereof.

Illustrated processing block 352, begins a registration process. Processing block 352 can seek identifying information of a user, such as name, email, etc. Personalized relief is determined via an initial registration stage where the user would undergo an initialization process. Illustrated processing block 354 executes a generic registration via generic training to expose the patient to sounds, images, videos, articles, etc. and determine via HRV reaction or manual (like/dislike) buttons what calms the user. Illustrated processing block 356 executes a voluntary assessments that asks the user to think of specific calming thoughts which can be of several categories. The categories can include place, person, animal, comedian, musician, album pictures, location, etc.

Figure 9:
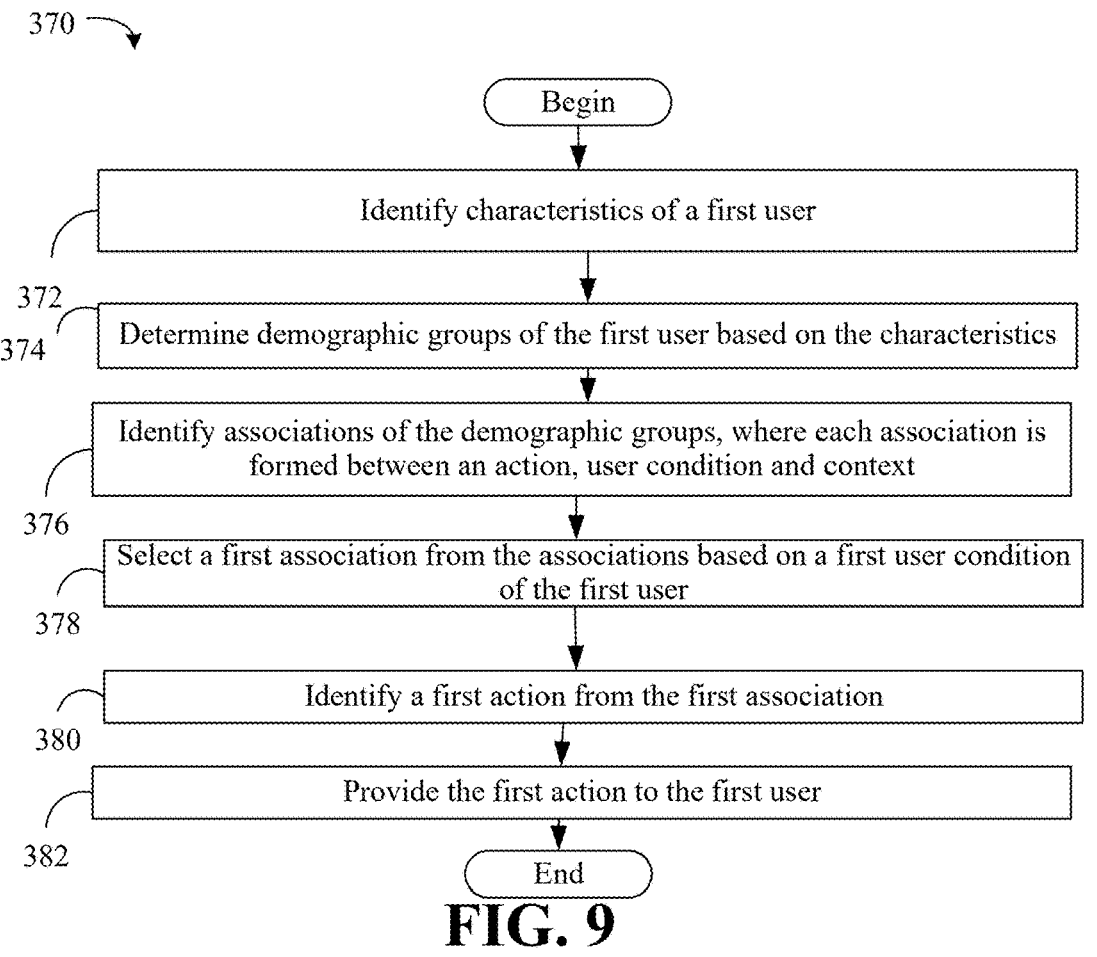
FIG. 9 is a flowchart of an example of identifying demographics of a user and actions based on the demographics according to an example.

FIG. 9 illustrates a method 370 of identifying demographics of a user and actions based on the demographics. The method 370 can generally be implemented in conjunction with any of the examples described herein, for example the respite process 100 (FIGS. 1A-1B), context identification and mental state remediation process 138 (FIGS. 2A-2B), method 250 (FIG. 3), and method 270 (FIG. 4), ANS diagram 290 (FIG. 5), HRV electrocardiogram 310 (FIG. 6), RMSSD calculation process 330 (FIG. 7), and method 350 (FIG. 8). In an example, the method 370 is implemented in logic instructions (e.g., software), configurable logic, fixed-functionality hardware logic, computer readable instructions stored on at least one non-transitory computer readable storage medium that are executable to implement method 370, circuitry, etc., or any combination thereof.

Illustrated processing block 372 identifies characteristics of a first user. Illustrated processing block 374 determines demographic groups of the first user based on the characteristics. Illustrated processing block 376 identifies associations of the demographic groups, where each association is formed between an action, user condition and context. Illustrated processing block 378 selects a first association from the associations based on a first user condition of the first user. Illustrated processing block 380 identifies a first action from the first association. Illustrated processing block 382 provides the first action to the first user.

Figure 10:
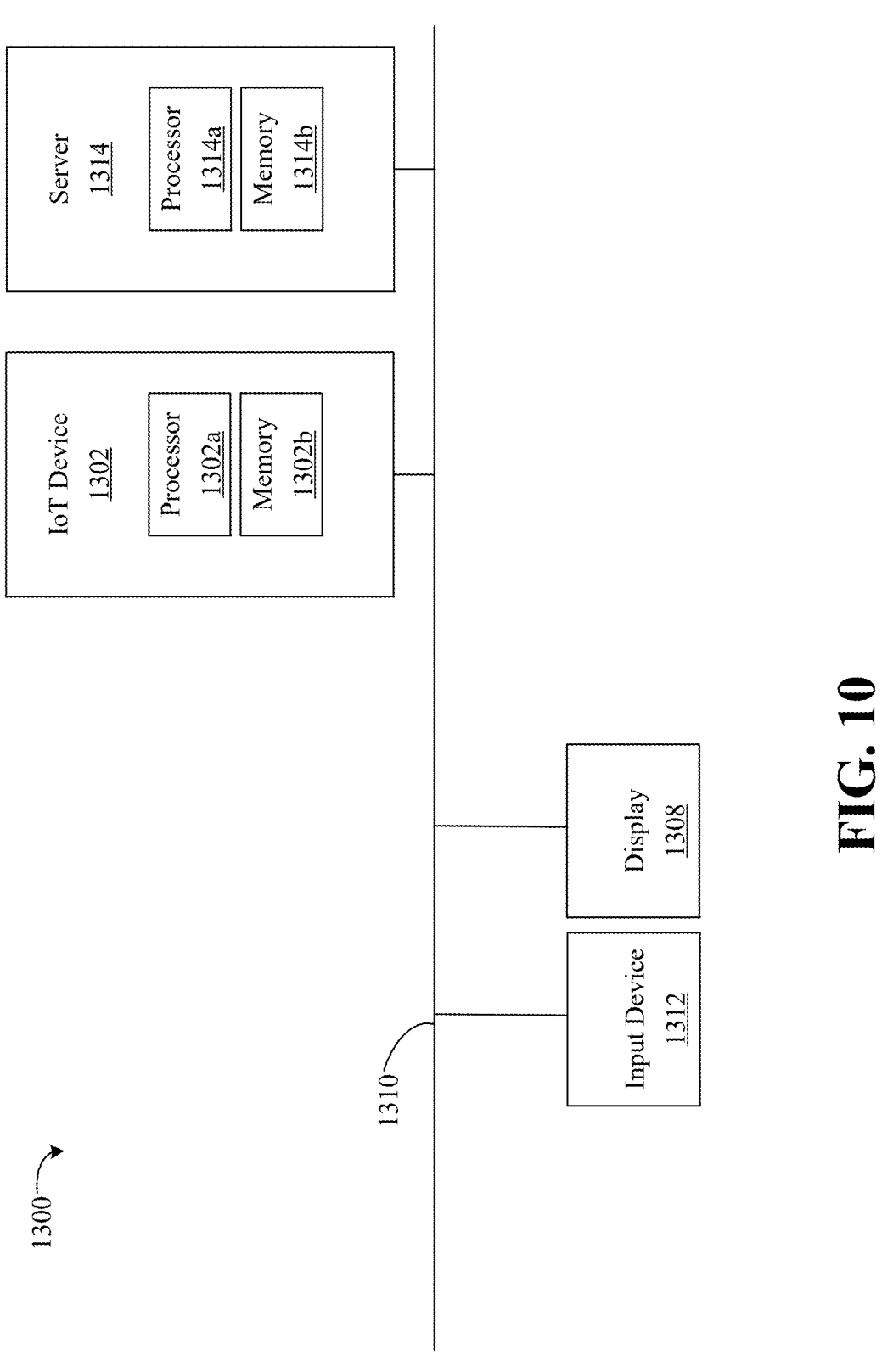
FIG. 10 is a block diagram of an example of a computing system according to an example.

FIG. 10 shows a more detailed example of a computing architecture 1300 to execute a respite process. The computing architecture 1300 can generally be implemented in conjunction with any of the examples described herein, for example respite process 100 (FIGS. 1A-1B), context identification and mental state remediation process 138 (FIGS. 2A-2B), method 250 (FIG. 3), and method 270 (FIG. 4), ANS diagram 290 (FIG. 5), HRV electrocardiogram 310 (FIG. 6), RMSSD calculation process 330 (FIG. 7), method 350 (FIG. 8) and method 370 (FIG. 9).

In the illustrated example, the computing architecture 1300 can include a network 1310 that can facilitate communicate between server 1314, IoT device 1302, input device 1312, and display 1308. The display 1308 (e.g., audio and/or visual interface) can present a browser and notifications to a user, and the input device 1312 can receive user inputs (e.g., demographic related data, survey answers, etc.).

A server 1314 includes a processor 1314a (e.g., embedded controller, central processing unit/CPU) and a memory 1314b (e.g., non-volatile memory/NVM and/or volatile memory) containing a set of instructions, which when executed by the processor 1314a, cause the server 1314 to implement aspects described herein, for example determining a user condition based on the received first data, determining a context associated with the user condition based on the received second data, determining a first action to mitigate the user condition based on the context, and providing the first action to a user device associated with the user, wherein the user device is to execute the first action.

The IoT device 1302 includes a processor 1302a (e.g., embedded controller, central processing unit/CPU) and a memory 1302_b_ (e.g., non-volatile memory/NVM and/or volatile memory) containing a set of instructions, which when executed by the processor 1302_a_, cause the IoT device 1302 to implement aspects described herein, for example transmitting sensed data to the server 1314. Multiple IoT devices can be included.

FIG. 11 illustrates a method 390 of identifying demographics of a user and actions based on the demographics. The method 390 can generally be implemented in conjunction with any of the examples described herein, for example the respite process 100 (FIGS. 1A-1B), context identification and mental state remediation process 138 (FIGS. 2A-2B), method 250 (FIG. 3), and method 270 (FIG. 4), ANS diagram 290 (FIG. 5), HRV electrocardiogram 310 (FIG. 6), RMSSD calculation process 330 (FIG. 7), method 350 (FIG. 8), method 370 (FIG. 9) and/or computing architecture 1300 (FIG. 10). In an example, the method 390 is implemented in logic instructions (e.g., software), configurable logic, fixed-functionality hardware logic, computer readable instructions stored on at least one non-transitory computer readable storage medium that are executable to implement method 390, circuitry, etc., or any combination thereof.

Illustrated processing block 392 receives first data and second data from an internet-of-things device associated with a user, where the first data includes a measurement of the user. Illustrated processing block 394 determines a user condition based on the received first data. Illustrated processing block 396 determines a context associated with the user condition based on the received second data. Illustrated processing block 398 determines a first action to mitigate the user condition based on the context. Illustrated processing block 400 provides the first action to a user device associated with the user, where the user device is to execute the first action.

In some examples, the user condition is one or more of anxiety, fear or anger. The internet-of-things device includes one or more of a smartwatch, an artificial intelligence voice assistant, a connected car, a speaker, a microphone, a mobile device, a computing device, a thermostat, a continuous glucose monitor or an imaging device. In some examples the first data includes one or more of a location, audio, a location of the user, or a velocity of the user.

In some examples, the method 390 includes receiving third data from the internet-of-things device, identifying the context from the third data, determining that a probability of the user condition occurring in the future is above a threshold based on the context being identified from the third data, identifying a second action to mitigate the user condition and based on the probability of the user condition occurring in the future being above the threshold, and controlling the user device to execute the second action. The method 390 can include repeatedly measuring a user characteristic of the user a plurality of times to receive a plurality of measurements, determining a baseline measurement for the user based on the plurality of measurements, and comparing the first data to the baseline measurement associated with the user. In some examples, the method 390 sets a threshold based on a past record of heart rate variability of the user, identifies a first heart variability rate of the user from the first data, identifies that the first heart variability rate is below a threshold, and determines that the user has the user condition based on the first heart variability rate being below the threshold. In some examples the method 390 includes accessing a past record of the user, identifying previous actions that mitigated previous conditions associated with the user based on the past record, and selecting the first action based on the previous actions and the user condition. The first action can include blocking an application on the user device from executing a task.

"COMPONENT" in this context refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example examples, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a Field-Programmable Gate Array (FPGA) or an ASIC. A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering examples in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In examples in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output.

Hardware components may also initiate communications with input or output devices and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some example examples, the processors or processor-implemented components may be located in a single geographic location (e.g., within a home environment, an office environment, or a server farm). In other examples, the processors or processor-implemented components may be distributed across a number of geographic locations.

The term "coupled" can be used herein to refer to any type of relationship, direct or indirect, between the components in question, and can apply to electrical, mechanical, fluid, optical, electromagnetic, electromechanical or other connections. In addition, the terms "first", "second", etc. can be used herein only to facilitate discussion, and carry no particular temporal or chronological significance unless otherwise indicated.

Those skilled in the art will appreciate from the foregoing description that the broad techniques of the examples of the present disclosure can be implemented in a variety of forms. Therefore, while the examples of this disclosure have been described in connection with particular examples thereof, the true scope of the examples of the disclosure should not be so limited since other modifications will become apparent to the skilled practitioner upon a study of the drawings, specification, and following claims.

We claim:

1. A computing system comprising:
a processor; and
a memory having a set of instructions, which when executed by the processor, cause the computing system to:
receive first data and second data from one or more first internet-of-things devices associated with a user, wherein the first data includes biological measurements of the user at different times, further wherein the second data includes previous events that occurred prior to each of the different times;
determine that the user experienced a user condition at each of the different times based on the biological measurements;
determine at least one common event from the previous events that occurred prior to each of the different times;
determine that the at least one common event is associated with the user interacting with an application on a user device associated with the user;
determine a first action to mitigate the user condition based on the at least one common event being associated with the user interacting with the application, wherein the first action blocks the application from executing on the user device;
receive third data from one or more second internet-of-things devices;
determine from the third data that a probability of the user condition occurring in the future is above a threshold;
provide the first action to the user device associated with the user based on the probability being above the threshold; and
execute, by the user device, the first action to block the application from executing on the user device.

2. The computing system of claim 1, wherein:
the user condition is one or more of anxiety, fear or anger;
the one or more first and second internet-of-things device includes one or more of a smartwatch, an artificial intelligence voice assistant, a connected car, a speaker, a microphone, a mobile device, a computing device, a continuous glucose monitor or an imaging device; and
the first data includes one or more of, an audio, a location of the user, or a velocity of the user.

3. The computing system of claim 1, wherein the instructions of the memory, when executed, cause the computing system to:
repeatedly measure a user characteristic of the user a plurality of times to generate a plurality of baseline biological measurements;
determine a baseline measurement for the user based on the plurality of baseline biological measurements; and
compare the first data to the baseline measurement associated with the user.

4. The computing system of claim 1, wherein the instructions of the memory, when executed, cause the computing system to:
set a threshold based on a past record of heart rate variability of the user;
identify a first heart variability rate of the user from the first data;
identify that the first heart variability rate is below a threshold; and
determine that the user has the user condition based on the first heart variability rate being below the threshold.

5. The computing system of claim 1, wherein the instructions of the memory, when executed, cause the computing system to:
access a past record of the user;

identify previous actions that mitigated previous conditions associated with the user based on the past record; and select the first action based on the previous actions and the user condition.

6. The computing system of claim 1, wherein the first internet-of-things devices are the same as the second internet-of-things devices.

7. The computing system of claim 1, wherein the first internet-of-things devices are different from the second internet-of-things devices.

8. At least one non-transitory computer readable storage medium comprising a set of instructions, which when executed by a computing system, cause the computing system to:

receive first data and second data from one or more first internet-of-things devices associated with a user, wherein the first data includes biological measurements of the user at different times, further wherein the second data includes previous events that occurred prior to each of the different times;

determine that the user experienced a user condition at each of the different times based on the biological measurements;

determine at least one common event from the previous events that occurred prior to each of the different times;

determine that the at least one common event is associated with the user interacting with an application on a user device associated with the user;

determine a first action to mitigate the user condition based on the at least one common event being associated with the user interacting with the application, wherein the first action blocks the application from executing on the user device;

receive third data from one or more second internet-of-things devices;

determine from the third data that a probability of the user condition occurring in the future is above a threshold;

provide the first action to the user device associated with the user based on the probability being above the threshold; and execute, by the user device, the first action to block the application from executing on the user device.

9. The at least one non-transitory computer readable storage medium of claim 8, wherein:

the user condition is one or more of anxiety, fear, sadness or anger;

the one or more first and second internet-of-things device includes one or more of a smartwatch, an artificial intelligence voice assistant, a connected car, a speaker, a microphone, a mobile device, a computing device a continuous glucose monitor or an imaging device; and the first data includes one or more of, an audio, a location of the user, or a velocity of the user.

10. The at least one non-transitory computer readable storage medium of claim 8, wherein the instructions, when executed, cause the computing system to:

repeatedly measure a user characteristic of the user a plurality of times to generate a plurality of baseline biological measurements;

determine a baseline measurement for the user based on the plurality of baseline biological measurements; and compare the first data to the baseline measurement associated with the user.

11. The at least one non-transitory computer readable storage medium of claim 8, wherein the instructions, when executed, cause the computing system to:

set a threshold based on a past record of heart rate variability of the user;

identify a first heart variability rate of the user from the first data;

identify that the first heart variability rate is below a threshold; and determine that the user has the user condition based on the first heart variability rate being below the threshold.

12. The at least one non-transitory computer readable storage medium of claim 8, wherein the instructions, when executed, cause the computing system to:

access a past record of the user;

identify previous actions that mitigated previous conditions associated with the user based on the past record; and select the first action based on the previous actions and the user condition.

13. The at least one non-transitory computer readable storage medium of claim 8, wherein the first internet-of-things devices are the same as the second internet-of-things devices.

14. The at least one non-transitory computer readable storage medium of claim 8, wherein the first internet-of-things devices are different from the second internet-of-things devices.

15. A method comprising:

receiving first data and second data from one or more first internet-of-things devices associated with a user, wherein the first data includes biological measurements of the user at different times, further wherein the second data includes previous events that occurred prior to each of the different times;

determining that the user experienced a user condition at each of the different times based on the biological measurements;

determining at least one common event from the previous events that occurred prior to each of the different times;

determining that the at least one common event is associated with the user interacting with an application on a user device associated with the user;

determining a first action to mitigate the at least one common event being associated with the user interacting with the application, wherein the first action blocks the application from executing on the user device;

receiving third data from one or more second internet-of-things devices;

determining from the third data that a probability of the user condition occurring in the future is above a threshold;

providing the first action to the user device associated with the user based on the probability being above the threshold; and executing, by the user device, the first action to block the application from executing on the user device.

16. The method of claim 15, wherein:

the user condition is one or more of anxiety, fear or anger;

the one or more first and second internet-of-things device includes one or more of a smartwatch, an artificial intelligence voice assistant, a connected car, a speaker, a microphone, a mobile device, a computing device, a continuous glucose monitor or an imaging device; and the first data includes one or more of, an audio, a location of the user, or a velocity of the user.

17. The method of claim 15, further comprising:

repeatedly measuring a user characteristic of the user a plurality of times to generate a plurality of baseline biological measurements;

determining a baseline measurement for the user based on the plurality of baseline biological measurements; and comparing the first data to the baseline measurement associated with the user, wherein the first internet-of-things devices are the same as the second internet-of-things devices.

18. The method of claim 15, further comprising:

setting a threshold based on a past record of heart rate variability of the user;

identifying a first heart variability rate of the user from the first data;

identifying that the first heart variability rate is below a threshold; and determining that the user has the user condition based on the first heart variability rate being below the threshold.

19. The method of claim 15, further comprising:

accessing a past record of the user;

identifying previous actions that mitigated previous conditions associated with the user based on the past record; and selecting the first action based on the previous actions and the user condition.

20. The method of claim 15, further wherein the first internet-of-things devices are different from the second internet-of-things devices.

* * * * *